(12) United States Patent
Roudebush

(10) Patent No.: US 8,541,245 B2
(45) Date of Patent: Sep. 24, 2013

(54) METHOD FOR ASSESSING OOCYTE MATURATION

(75) Inventor: William E. Roudebush, Chanhassen, MN (US)

(73) Assignee: Beckman Coulter, Inc., Brea, CA (US)

( * ) Notice: Subject to any disclaimer, the term of this patent is extended or adjusted under 35 U.S.C. 154(b) by 320 days.

(21) Appl. No.: 12/814,038

(22) Filed: Jun. 11, 2010

(65) Prior Publication Data

US 2011/0111523 A1 May 12, 2011

Related U.S. Application Data

(60) Provisional application No. 61/186,755, filed on Jun. 12, 2009.

(51) Int. Cl.
*G01N 33/53* (2006.01)
*C07K 1/00* (2006.01)

(52) U.S. Cl.
USPC ............... 436/510; 436/548; 436/8; 436/15; 436/63; 436/87; 436/814; 436/818; 436/906; 435/7.1; 435/806; 530/313; 530/395; 530/397; 530/398; 530/400

(58) Field of Classification Search
USPC ............. 435/6, 7.1, 806; 436/507, 510, 548, 436/8, 15, 16, 814, 818, 906, 907, 63, 87; 530/513, 395, 397, 398, 400, 313
See application file for complete search history.

(56) References Cited

U.S. PATENT DOCUMENTS 5,075,212 A 12/1991 Rotbart

OTHER PUBLICATIONS

Qin et al. Double-monoclonal immunofluorescent assays for pregnancy-associated plasma protein A / proeosinophil major basic protein (PAPP-A/proMBP) complex in first-trimester maternal serum screening for Down syndrome, Clinical Chemistry 43:12 (2323-2332 (1997).*
Batzer et al., "Enhanced evolutionary PCR using oligonucleotides with inosine at the 3'-terminus" Nucleic Acid Research 19:5081; Oxford University Press (1991).
Ohtsuka et al., "An Alternative Approach to Deoxyoligonucleotides as Hybridization Probes by Insertion of Deoxyinosine at Ambiguous Codon Positions", J. Biol. Chem. 260:2605-2608 (1985).
Rossolini et al., "Use of deoxyinosine-containing primers vs degenerate primers for polymerase chain reaction based on ambiguous sequence information", Mol. Cell. Probes 8:91-98 (1994).
Leicher et al., "Coexpression of the KCNA3B Gene Product with Kv1.5 Leads to a Novel A-type Potassium Channel", J. Biol. Chem. 273(52):35095-35101 (1998).
Chandrasekher et al., "Estrogen- But Not Androgen-Dominant Human Ovarian Follicular Fluid Contains an Insulin-Like Growth Factor Binding Protein-4 Protease", J.Clin. Endocrinol. Metab., 80:2734-2739 (1995).
Qin et al., "Double-monoclonal immunofluorometric assays for preganancy-associated plasma proten A/proeosinophil major basic protein (PAPP-A/proMBP) complex in first-trimester maternal serum screening for Down syndrome", Clin. Chem., 43(12):2323-2332, (1997).

(Continued)

*Primary Examiner* — Gail R Gabel
(74) *Attorney, Agent, or Firm* — Merchant & Gould P.C.

(57) ABSTRACT

The present invention provides methods and kits for assessing the state of oocyte maturation in a female mammal based on the level of PAPP-A found in the female's bodily fluid sample.

23 Claims, 14 Drawing Sheets

(56) References Cited

OTHER PUBLICATIONS

Kohler G. et al., "Continuous cultures of fused cells secreting antibody of predefined specificity", Nature, 256:495 (1975).
Kozbor et al., "The production of monoclonal antibodies form human lymphocytes", Immunology Today, 4(3):72 (1983).
Cole et al., "Generation of human monoclonal antibodies reactive with cellular antigens", Proc. Natl. Acad. Sci., USA, 80:2026-2030 (1983).
Huse et al., "Generation of a Large combinatorial Library of the Immunoglobulin Repertoire in Phage Lambda", Science, 246:1275 (1989).
Romero et al., "PCR Detection of the Human Enteroviruses", Diagnostic Molecular Biology: Principles and Applications, pp. 401-406, (2003).
Egger et al., "Reverse Transcription Multiplex PCR for Differentiation between Polio- and Enteroviruses from Clinical and Environmental Samples", J. Clin. Microbiol. 33(6):1442-1447, (1995).
Nolte, Frederick S., "Branced DNA Signal Amplification for Direct Quantitation of Nucleic Acid Sequences in Clinical Speciments", Adv. Clin. Chem. 33:201-235, (1998).
Singer et al., "Optimization of in situ Hybridization Using Isotopic and non-Isotopic Detection Methods", Biotechniques 4(3):230, (1986).
Haase et al., "Detection of Viral Nucleic Acids by in Situ Hybridization", Methods in Virology, vol. VII, 189-226, (1984).
Beaucage et al., "Deoxynucleoside Phosphoramidites—A New Class of Key Intermediates for Deoxypolynucleotide Synthesis" Tetrahedron Letts., 22(20):1859-1862, (1981).
Needham-Vandevanter et al., "Characterization of an adduct between CC-1065 and a defined oligodeoxynucleotide duplex", Nucleic Acids Res. 12(15):6159-6168, (1984).
Pearson et al., "High-Performance Anion-Exchange Chromatagraphy of Oligonucleotides", J. Chrom., 255:137-149, (1983).

* cited by examiner

FIG. 1A

| Name | 1 | 3 | 6 | 8 | 10 | 11 | 12 | 13 | 16 | 17 | 18 | 19 | 22 | 24 | 15 | 14 |
|---|---|---|---|---|---|---|---|---|---|---|---|---|---|---|---|---|
| Age | 32 | 23 | 35 | 33 | 31 | 31 | 30 | 31 | 31 | 34 | 33 | 34 | 33 | 29 | 33 | 26 |
| FSH Dose | 4550 | 2625 | 3000 | 1500 | 700 | 750 | 1050 | 3300 | 225 | 1300 | 2750 | 900 | 1350 | 413 | 450 | 2175 |
| #ET | 0 | 0 | 3 | 2 | 2 | 2 | 2 | 3 | 2 | 2 | 3 | 2 | 2 | 2 | 2 | 3 |
| [FMF] on hCG Day | 1.2 | 2.1 | 2.1 | 1.8 | 2.1 | 1.7 | 1.2 | 2.8 | 1.7 | 1.5 | 2.3 |  | 2.1 | 2.1 | 1.9 | 1.1 |
| Date | 1/19/2007 | 1/20/2007 | 1/26/2007 | 1/27/2007 | 1/29/2007 | 1/30/2007 | 1/31/2007 | 1/29/2007 | 1/27/2007 | 1/27/2007 | 2/4/2007 | 1/30/2007 | 2/3/2007 | 2/3/2007 | 1/27/2007 | 1/27/2007 |
| Follicle Count | 24 | 25 | 4 | 18 | 32 | 19 | 30 | 9 | 61 | 16 | 8 | 21 | 11 | 22 | 4 | 24 |
| follicle >1.4 | 10 | 11 | 2 | 9 | 13 | 17 | 18 | 7 | 20 | 8 | 3 | 12 | 10 | 11 | 2 | 9 |
| hCG Day | 13 | 11 | 12 | 11 | 9 | 9 | 10 | 11 | 10 | 14 | 12 | 10 | 10 | 10 | 14 | 9 |
| #Eggs | 15 | 15 | 3 | 18 | 22 | 19 | 33 | 8 | 22 | | 5 | 18 | 9 | 15 | 3 | 25 |
| [FMF] per follicle | 0.05 | 0.08 | 0.53 | 0.10 | 0.07 | 0.09 | 0.04 | 0.31 | 0.03 | 0.09 | 0.29 | 0.14 | 0.19 | 0.10 | 0.48 | 0.05 |
| [FMF] per follicle >1.4 | 0.12 | 0.19 | 1.05 | 0.20 | 0.16 | 0.10 | 0.07 | 0.40 | 0.09 | 0.19 | 0.77 | 0.25 | 0.21 | 0.19 | 0.95 | 0.12 |
| [FMF] per egg | 0.08 | 0.14 | 0.70 | 0.10 | 0.10 | 0.09 | 0.04 | 0.35 | 0.08 | 0.11 | 0.46 | 0.17 | 0.23 | 0.14 | 0.63 | 0.04 |
| #designated ICSI | 15 | 0 | 3 | 9 | 11 | 10 | 11 | 8 | 11 | 7 | 5 | 18 | 5 | 8 | 3 | 6 |
| #1pb | 13 | 9 | 2 | 4 | 9 | 8 | 8 | 7 | 10 | 4 | 5 | 9 | 4 | 6 | 2 | 6 |
| MR | 0.867 | 0.6 | 0.667 | 0.222 | 0.409 | 0.421 | 0.242 | 0.875 | 0.455 | 0.286 | – | 0.5 | 0.444 | 0.4 | 0.667 | 0.24 |
| [FMF] per 1pb | 0.09 | 0.23 | 1.05 | 0.45 | 0.23 | 0.21 | 0.15 | 0.40 | 0.17 | 0.38 | 0.46 | 0.33 | 0.53 | 0.35 | 0.95 | 0.18 |
| #0pb | 2 | 3 | 1 | – | 0 | – | 0 | – | – | 0 | 0 | 3 | 0 | 0 | 0 | 0 |
| #GV | 0 | 3 | 0 | 1 | 2 | – | 3 | 0 | 0 | 3 | – | 5 | – | 1 | – | – |
| #CONV | 0 | 0 | 0 | 3 | 11 | 9 | 22 | – | 11 | 7 | – | 0 | 4 | 7 | 0 | 0 |
| pos HCG | 0 | 0 | 1 | 9 | – | – | – | – | – | – | – | 0 | 0 | 0 | 0 | 0 |
| Comments | NO ET, FREEZE ALL | NO ET, FREEZE ALL | | 1 EGG DESIGNATED ICSI WAS AN EMPTY ZONA | | | | | PCOS | | | 1 EGG DESIGNATED ICSI WAS AN FZP | 1 EGG DESIGNATED ICSI WAS AN EMPTY ZONA | | 1 EGG DESIGNATED ICSI WAS AN EMPTY ZONA | ONLY 6 EGGS GIVEN TO RECIP., OF THE 25 TOTAL EGGS FROM DONOR 12 WERE 1PB, 3 WERE 0pb, AND 10 WERE GV's |

IVF Sample Testing for PAPP-A
*prepared for Bill Rousdebush*

| Patient # | Draw Date | Dose (ng/mL) |
|---|---|---|
| 001 | 1/12/07 | 1.3 |
| | 1/13/07 | 1.3 |
| | 1/14/07 | 1.3 |
| | 1/15/07 | 1.2 |
| | 1/16/07 | 1.3 |
| | 1/17/07 | 1.2 |
| 002 | 1/13/07 | 2.3 |
| | 1/14/07 | 2.5 |
| | 1/15/07 | 2.7 |
| | 1/16/07 | 2.9 |
| | 1/17/07 | 2.8 |
| | 1/18/07 | 2.4 |
| 003 | 1/13/07 | 2.3 |
| | 1/14/07 | 2.4 |
| | 1/15/07 | 2.3 |
| | 1/18/07 | 2.1 |
| 004 | 1/13/07 | 2.1 |
| | 1/14/07 | 2.3 |
| | 1/15/07 | 2.4 |
| | 1/16/07 | 2.5 |
| | 1/17/07 | 2.3 |
| 005 | 1/20/07 | 3.1 |
| | 1/22/07 | 3.4 |
| | 1/23/07 | 3.0 |
| | 1/24/07 | 2.6 |
| 006 | 1/19/07 | 2.3 |
| | 1/20/07 | 2.1 |
| | 1/21/07 | 2.4 |
| | 1/22/07 | 2.6 |
| | 1/23/07 | 2.4 |
| | 1/24/07 | 2.1 |
| 007 | 1/19/07 | 2.0 |
| | 1/21/07 | 1.9 |
| | 1/22/07 | 1.9 |
| | 1/23/07 | 1.7 |
| 008 | 1/19/07 | 1.9 |
| | 1/21/07 | 1.9 |
| | 1/22/07 | 1.8 |
| | 1/23/07 | 2.0 |
| | 1/24/07 | 1.7 |
| | 1/25/07 | 1.8 |
| 009 | 1/20/07 | 2.6 |
| | 1/22/07 | 2.5 |
| | 1/24/07 | 2.7 |
| 010 | 1/23/07 | 2.4 |
| | 1/25/07 | 2.2 |
| | 1/24/07 | 2.4 |
| | 1/26/07 | 2.1 |
| | 1/27/07 | 2.1 |
| 011 | 1/23/07 | 2.2 |
| | 1/24/07 | 2.1 |
| | 1/25/07 | 1.8 |
| | 1/26/07 | 1.9 |
| | 1/27/07 | 1.8 |
| | 1/28/07 | 1.7 |
| 012 | 1/19/07 | 2.3 |
| | 1/23/07 | 1.9 |
| | 1/24/07 | 2.1 |
| | 1/25/07 | 2.0 |
| | 1/26/07 | 1.7 |
| | 1/27/07 | 1.5 |
| | 1/28/07 | 1.2 |
| | 1/29/07 | 1.2 |
| 013 | 1/22/07 | 3.6 |
| | 1/20/07 | 3.0 |
| | 1/22/07 | 3.2 |
| | 1/24/07 | 3.0 |
| | 1/23/07 | 2.8 |
| 014 | 1/25/07 | 1.0 |
| | 1/22/07 | 0.8 |
| | 1/23/07 | 1.1 |
| | 1/24/07 | 1.1 |
| | 1/25/07 | 1.1 |
| 015 | 1/20/07 | 2.5 |
| | 1/22/07 | 1.9 |
| | 1/24/07 | 2.1 |
| | 1/25/07 | 1.9 |

| Patient # | Draw Date | Dose (ng/mL) |
|---|---|---|
| 016 | 1/20/07 | 2.6 |
| | 1/22/07 | 3.0 |
| | 1/23/07 | 2.1 |
| | 1/24/07 | 2.1 |
| | 1/25/07 | 1.7 |
| 017 | 1/22/07 | 2.1 |
| | 1/23/07 | 1.6 |
| | 1/24/07 | 2.5 |
| | 1/25/07 | 1.5 |
| 018 | 1/23/07 | 1.8 |
| | 1/25/07 | 1.6 |
| | 1/26/07 | 1.9 |
| | 1/28/07 | 1.9 |
| | 1/29/07 | 2.2 |
| | 1/30/07 | 3.2 |
| | 1/31/07 | 2.3 |
| | 2/1/07 | 2.8 |
| | 2/2/07 | 2.3 |
| 019 | 1/24/07 | 3.3 |
| | 1/25/07 | 3.1 |
| | 1/26/07 | 3.4 |
| | 1/27/07 | 3.3 |
| | 1/28/07 | 3.0 |
| 020 | 1/19/07 | 1.6 |
| | 1/20/07 | 1.7 |
| | 1/21/07 | 1.8 |
| | 1/22/07 | 1.8 |
| | 1/23/07 | 1.8 |
| 021 | 1/21/07 | 2.3 |
| | 1/24/07 | 2.4 |
| | 1/26/07 | 2.2 |
| | 1/28/07 | 1.9 |
| | 1/29/07 | 1.8 |
| 022 | 1/24/07 | 2.3 |
| | 1/27/07 | 2.4 |
| | 1/29/07 | 2.6 |
| | 1/30/07 | 2.3 |
| | 1/31/07 | 2.0 |
| | 2/1/07 | 2.1 |
| 023 | 1/25/07 | 1.1 |
| | 1/27/07 | 1.2 |
| | 1/28/07 | 1.2 |
| 024 | 1/28/07 | 2.3 |
| | 1/29/07 | 2.7 |
| | 1/30/07 | 2.3 |
| | 1/31/07 | 2.2 |
| | 2/1/07 | 2.1 |
| 025 | 1/26/07 | 1.5 |
| | 1/30/07 | 1.5 |
| | 2/1/07 | 1.3 |
| | 2/3/07 | 1.3 |
| | 2/4/07 | 1.3 |
| | 2/5/07 | 1.4 |
| 026 | 1/25/07 | 2.4 |
| | 1/29/07 | 2.1 |
| | 1/31/07 | n/a-sys err |
| | 2/2/07 | 1.9 |
| | 2/4/07 | 2.1 |
| | 2/5/07 | 1.9 |
| | 2/6/07 | 1.5 |
| | 2/7/07 | 1.4 |
| 027 | 1/28/07 | 2.5 |
| | 1/30/07 | 2.5 |
| | 2/1/07 | 2.4 |
| | 2/3/07 | 2.7 |
| | 2/5/07 | 2.1 |
| | 2/7/07 | 2.3 |
| | 2/8/07 | 2.5 |
| | 2/9/07 | 2.5 |
| 028 | 1/28/07 | 1.2 |
| | 1/30/07 | 1.1 |
| | 2/1/07 | 1.2 |
| | 2/2/07 | 1.4 |
| 029 | 1/31/07 | 2.4 |
| | 2/2/07 | 2.7 |
| | 2/3/07 | 2.5 |
| | 2/4/07 | 2.6 |
| | 2/5/07 | 2.3 |
| | 2/6/07 | 2.3 |

| Run Information | |
|---|---|
| Assay Name: | FMF (v12.52) |
| Instrument: | Access Base #400651 |
| Dates Run: | 4/12/07-4/16/07 |
| Tech: | Brianne Bilyeu |
| Reference: | LBN: 5366;041207 |
| | DB: 7098 |

FIG. 3

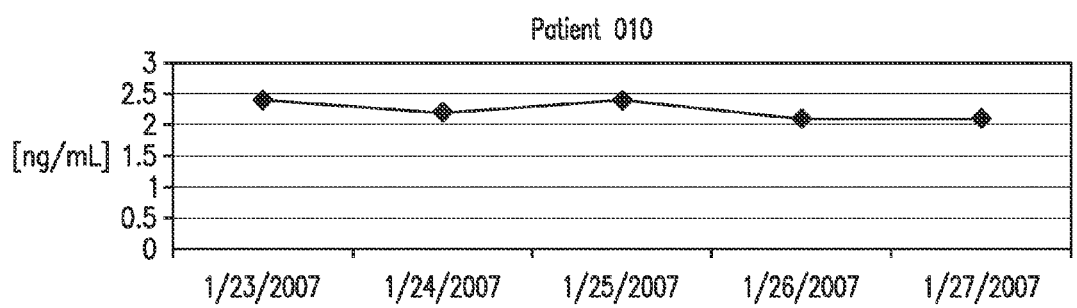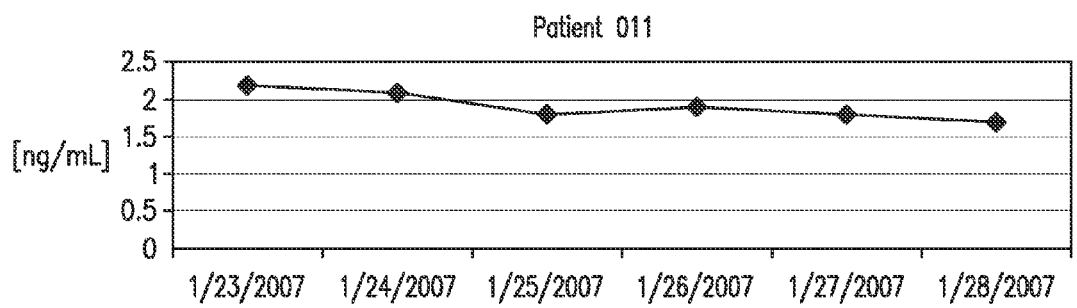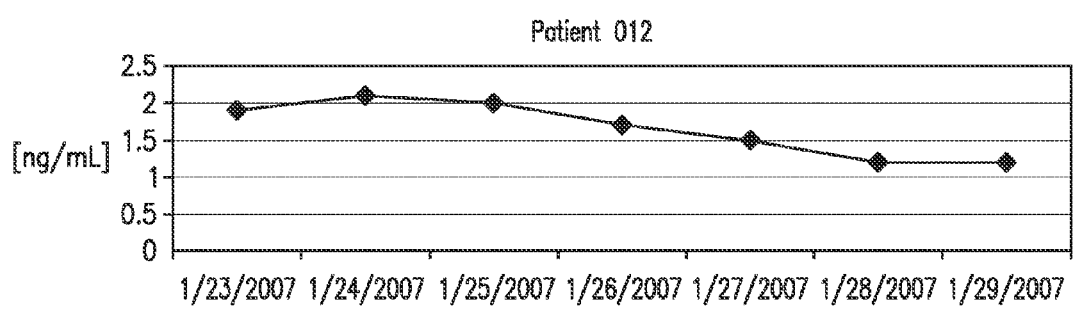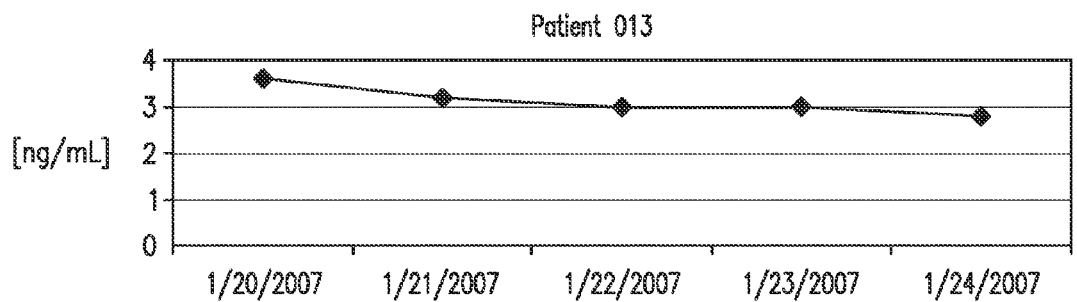
FIG. 4B

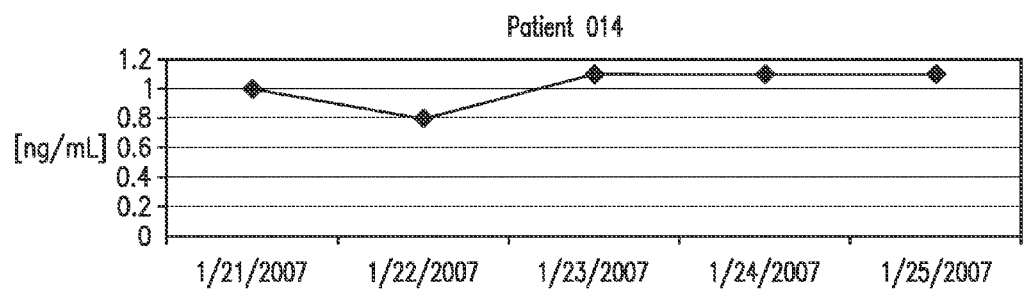
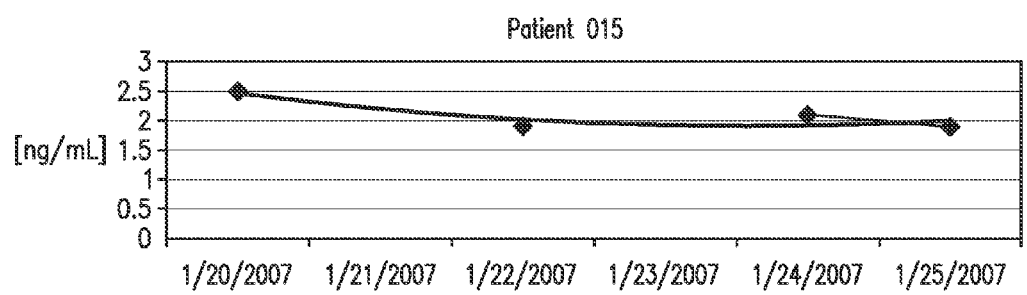
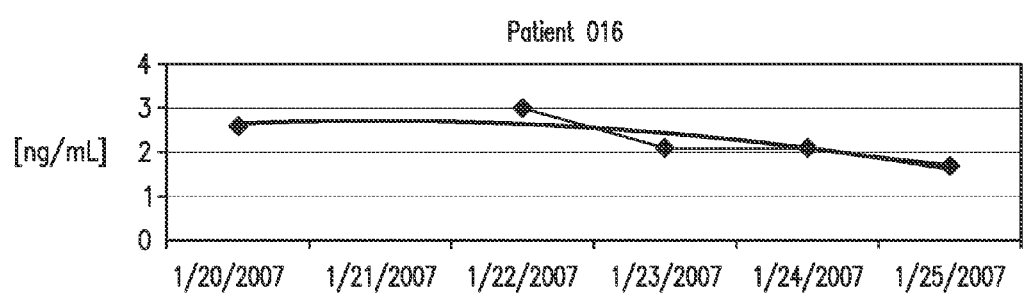
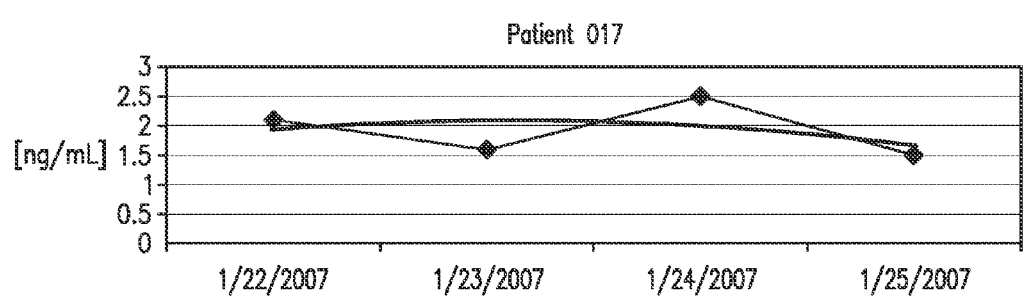
FIG. 4C

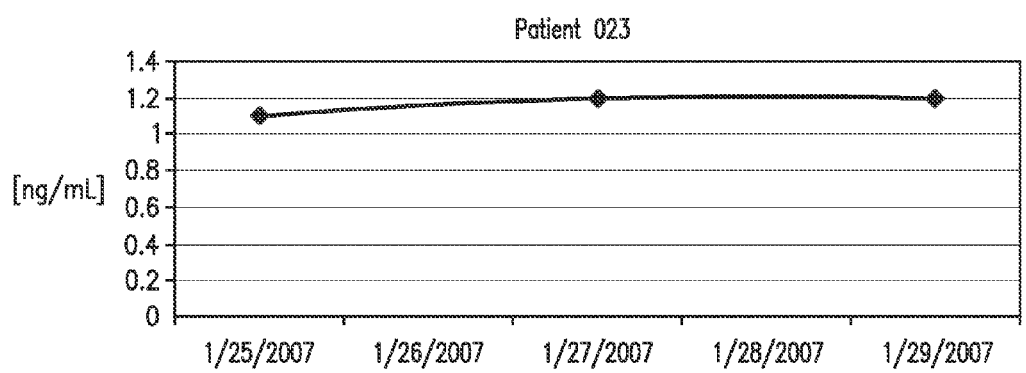
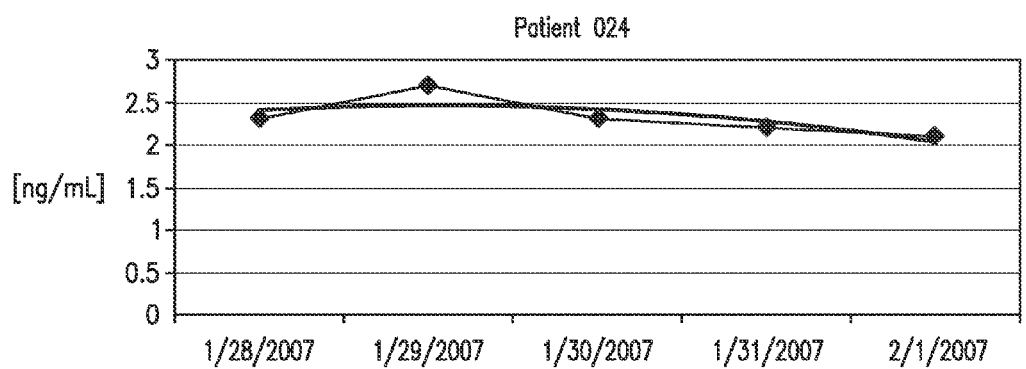
FIG. 4E

METHOD FOR ASSESSING OOCYTE MATURATION

BACKGROUND

According to the National Center for Health Statistics of the Centers for Disease Control and Prevention, about 12 percent of women (over 7.3 million) in the United States between the age 15-44 suffer from various fertility disorders, defined as difficulty getting pregnant or carrying a baby to term. Treatment of female infertility is therefore an important objective among health care professionals.

In placental mammals, each reproductive cycle consists of two phases: the follicular phase and the luteal phase. During the follicular phase, follicles undergo a maturation process and produce one or more ovum (also referred to as egg or oocyte). The release of mature egg(s) is called ovulation, a point that defines the transition from the follicular phase to the luteal phase. A successful conception requires the timely encounter of sperm and a mature egg. The ability of accurately predicting the time of ovulation is therefore highly beneficial in terms of providing a time frame to perform insemination with enhanced success rate. On the other hand, the ability of assessing oocyte maturation state in a female is also highly beneficial in the context of in vitro fertilization (IVF), a procedure that requires the extraction of eggs from maturing follicles from a female and is directly impacted in its success rate by the quality of the eggs. For the purpose of IVF, the current protocol for determining the time to carry out the steps of promoting final maturation of the eggs (by administration of human chorionic gonadotropin, or hCG, to the female) and harvesting eggs involves ultrasound, CT-scan, and some estimation, the method is therefore in need of improvement in both accuracy and efficiency.

Because of the high prevalence of female infertility and limitations in the current IVF technologies, there exists a need for new, effective, and convenient methods for assessing oocyte maturation and timing ovulation in reproductive medicine. The present invention addresses this and other related needs.

SUMMARY

In one aspect, this application provides a method for assessing oocyte maturation in a female. The method comprises the step of detecting pregnancy-associated plasma protein (PAPP-A) level in a bodily fluid from the female. The suitable bodily fluid may be follicular fluid or serum. In some embodiments of the method, the PAPP-A level is compared with a standard control, and an increase from the control indicates a more advanced state of oocyte maturation whereas a decrease from the control indicates a lesser state of oocyte maturation. In other embodiments, the step of detecting the PAPP-A level is performed in an immunoassay using an anti-PAPP-A antibody. Suitable anti-PAPP-A antibody for used in the claimed method may be a monoclonal antibody or a polyclonal antibody.

In some cases, the step of detecting the PAPP-A level is performed daily for a period of at least three days. For example, the PAPP-A level from each day is compared to monitor changes in oocyte maturation in the female, with a higher PAPP-A level indicating a more advanced state of oocyte maturation. In some embodiments, the claimed method further comprises the step of administering to the female chorionic gonadotropin (CG) or luteinizing hormone (LH) in an amount sufficient to induce oocyte maturation, and the step is performed within 36 hours or 24 hours after the PAPP-A level shows a decrease after continuous increase for at least two consecutive days. Optionally, a further step of collecting oocytes from the female is performed subsequent to the step of administering chorionic gonadotropin or luteinizing hormone. In some cases, the claimed method is performed on a human female, and the chorionic gonadotropin or luteinizing hormone is human chorionic gonadotropin (hCG) or human luteinizing hormone (hLH).

In some cases, the PAPP-A level used in the claimed method is the level reflecting the total amount of PAPP-A protein, which includes the amount of PAPP-A protein in its free form (i.e., homodimer) and the amount of PAPP-A protein in the heterotetramer form with the proform of eosinophil major basic protein (proMBP). In other cases, the PAPP-A level is either the amount of PAPP-A protein in its free form or the amount of PAPP-A protein in the PAPP-A/proMBP heterotetramer complex.

In a second aspect, the present invention provides a kit for assessing oocyte maturation in a female. The kit comprises (1) an agent that specifically binds pregnancy-associated plasma protein (PAPP-A) and (2) a standard control representing the average level of PAPP-A in a biological sample from a healthy female. In some embodiments, the kit may include multiple standard controls representing the average levels of PAPP-A in a particular biological sample from a healthy female on different days during the reproductive cycle; or the kit may include multiple standard controls representing the average levels of PAPP-A in different biological samples from a healthy female.

In some cases, the agent that specifically binds PAPP-A is an anti-PAPP-A antibody, which may be a monoclonal antibody or a polyclonal antibody. Optionally, the kit may include a second antibody, which has a binding specificity for the anti-PAPP-A antibody and comprises a detectable label. In many cases, the claimed kit will include user instruction material for using the kit.

The present invention is useful for the purpose of facilitating pregnancy in mammalian females, including primate, especially human, females. Typically, the subjects are adult females, frequently adult females of reproductive age, in some instances adult females desiring to become pregnant, in still further instances adult females undergoing medical intervention due to inability to become pregnant after at least 6 months of trying to become pregnant, and sometimes adult females undergoing ovulation induction.

DESCRIPTION OF THE DRAWINGS

FIG. 1A shows circulating PAPP-A protein levels in follicular fluid in individual patients with corresponding IVF data.

FIG. 3 presents serum PAPP-A levels in women over a period of at least 5 days around the time that hCG was given.

FIGS. 4A-E show serum PAPP-A levels in one pool of women over a period of at least 5 days.

DEFINITIONS

Figure 1B:
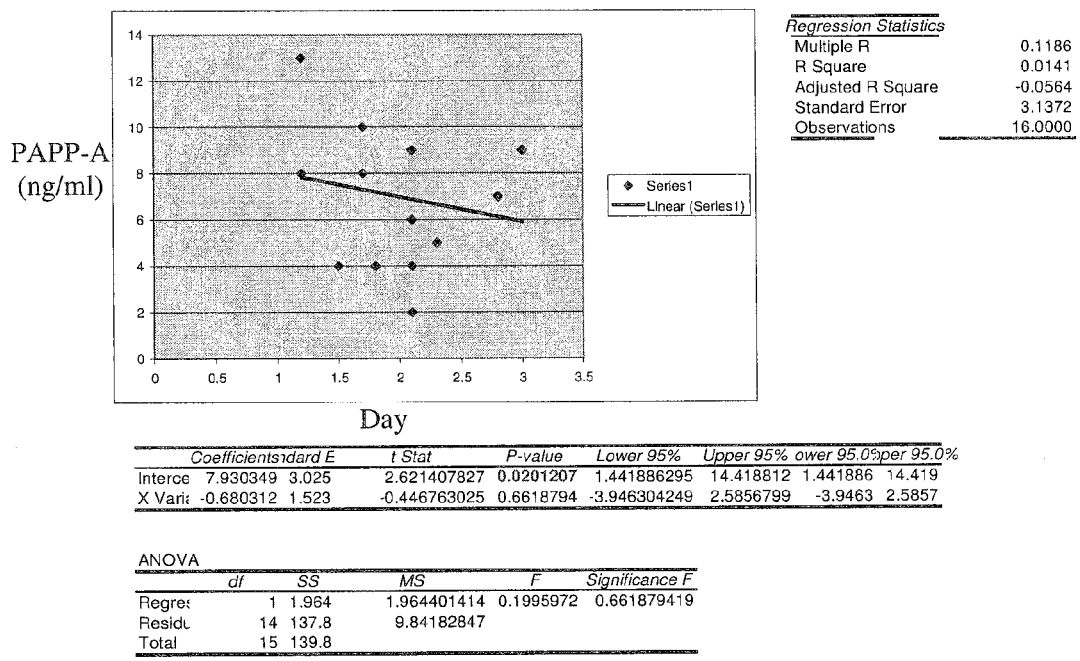
FIG. 1B shows the significant relationship (regression analysis and ANOVA) of PAPP-A levels to day that hCG was given.

As used herein, the term "pregnancy-associated plasma protein" or "PAPP-A" refers to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, or greater than about 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, preferably up to the entire length, of a polypeptide encoded by a respectively referenced nucleic acid or an amino acid sequence described herein, for example, as depicted in GenBank Accession No. X68280 (human PAPP-A mRNA) and Swiss-Prot. No. Q13219 (human PAPP-A protein); (2) specifically bind to antibodies, e.g., polyclonal antibodies, raised against an immunogen comprising a referenced amino acid sequence as depicted in Swiss-Prot. No. Q13219 (human PAPP-A protein); immunogenic fragments respectively thereof, and conservatively modified variants respectively thereof; (3) specifically hybridize under stringent hybridization conditions to a nucleic acid encoding a referenced amino acid sequence as depicted in Swiss-Prot. No. Q13219 (human PAPP-A protein), respectively, and conservatively modified variants respectively thereof; (4) have a nucleic acid sequence that has greater than about 95%, preferably greater than about 96%, 97%, 98%, 99%, or higher nucleotide sequence identity, preferably over a region of at least about 25, 50, 100, 150, 200, 250, 500, 1000, or more nucleotides, to a reference nucleic acid sequence as shown in GenBank Accession No. X68280 (human PAPP-A mRNA). A polynucleotide or polypeptide sequence for PAPP-A is from a mammal including, but not limited to, primates (e.g., human), rodents (rat, mouse, hamster, etc.), cows, pigs, horses, sheep/goats, or any other mammals. The PAPP-A nucleic acids and proteins useful for the invention include both naturally occurring or recombinant molecules. Furthermore, since PAPP-A protein may exist in the complex form of heterotetramer with the proform of eosinophil major basic protein (proMBP) or in the free form of homodimer, the term "PAPP-A protein" in this application encompasses all forms of PAPP-A, bound and unbound, unless a particular form is specified.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to VH-CH1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The term "average," as used in the context of describing a healthy, non-pregnant female mammal, i.e., one who is not suffering from any known fertility disorder, refers to certain characteristics, such as the level of PAPP-A protein or mRNA found in the subject's bodily fluids (e.g., whole blood, serum, plasma, and follicular fluid) that are representative of a randomly selected group of non-pregnant females not suffering from or at risk of developing any fertility disorder. This selected group typically comprises a sufficient number of female individuals such that the average level of PAPP-A among these individuals reflects, with reasonable accuracy, the level of PAPP-A in the general population of healthy females who are non-pregnant and free of fertility disorders. In addition, the selected group of individuals may, optionally, have similar aspects in medical history, as well as in age and genetic background, etc.; while in other cases no such similarity is required for establishing an average amount of circulating PAPP-A protein or mRNA.

"Standard control" as used herein refers to a sample suitable for the use as a comparison basis in a method of the present invention, in order for determining whether an increase or decrease exists in the amount of PAPP-A protein or mRNA found in a sample from a female subject, e.g., in the serum sample or follicular fluid sample. Such sample contains a known amount of the PAPP-A protein or mRNA that closely reflects the average level of PAPP-A protein or mRNA in an average female individual who is not suffering from a fertility disorder or at risk of developing such a disorder, as described above. In some cases, a "standard control" is reflective of the average PAPP-A level at a particular point of time, e.g., a particular day, during an average female's reproductive cycle (i.e., menstrual or estrous cycle). In other cases, especially when the method of this invention is used in the context of monitoring change of egg maturation status in a female subject, a "standard control" may be reflective of a baseline value of PAPP-A level for this particular female individual, e.g., at any particular point of time (a particular day) during the menstrual cycle.

"An increase or a decrease from the standard control" as used herein refers to a positive or negative change in amount from the standard control. An increase is typically at least 10%, or at least 20%, or 50%, or 100%, or at least 2-fold, or at least 5-fold, and can be as high as at least 10-fold or even 20-fold. Similarly, a decrease is typically at least 50%, or at least 80%, or at least 90%, or even as high as more than 99% in reduction from the level of standard control.

As used here, the term "reproductive cycle" refers to a recurring cycle of physiologic changes that takes place in reproductive-age female mammals. This term encompasses both menstrual cycle in human and evolutionarily closely related primates (such as chimpanzees) that have an overt menstruation phase during their cycles, and estrous cycle in other species of placental mammals that do not have an overt menstruation phase during the cycle.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"PCR primers" as used herein refer to oligonucleotides, typically in pairs, that can be used in a polymerase chain reaction (PCR) to amplify a nucleotide sequence originated from an mRNA encoding a protein of interest, such as human PAPP-A. Typically, at least one of the PCR primers for amplification of a nucleotide sequence encoding a PAPP-A protein should be sequence-specific for the protein.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "biological sample" includes any section of tissues such as biopsy and autopsy samples, and frozen sections taken for histological purposes. Such samples include blood and blood fractions or products (e.g., serum, plasma, platelets, red blood cells, and the like), other bodily fluids (such as urine, saliva, oral washings, reproductive tract washings, and sweat), sputum, tissue, cultured cells, e.g., primary cultures, explants, and transformed cells, stool, urine, etc. A biological sample of this invention is obtained from a mammal such as a primate (e.g., chimpanzee or human); cow; dog; cat; rodent (e.g., guinea pig, rat, or mouse); rabbit; and the like.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., prostate, lymph node, liver, bone marrow, blood cell), the size and type of the tumor (i.e., solid or suspended (i.e., blood or ascites)), among other factors. Representative biopsy techniques include excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The phrase "specifically binds," when referring to a protein or peptide, refers to a binding reaction that is determinative of the presence of the protein in a heterogeneous population of proteins and other biologics. Thus, under designated immunoassay conditions, the specified binding agent, e.g., an antibody, binds to a particular protein at least two times the background and does not substantially bind in a significant amount to other proteins present in the sample. Specific binding to an antibody under such conditions may require an antibody that is selected for its specificity for a particular protein or a protein in a particular form. For example, antibodies may be raised to specifically bind PAPP-A protein including both the complex with proMBP and PAPP-A free form. In the alternative, antibodies can be raised and selected to specifically bind the PAPP-A/proMBP complex. In another alternative, antibodies may be selected to specifically bind PAPP-A in its free form. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background.

DESCRIPTION

I. Introduction

Pregnancy-associated plasma protein (PAPP-A) is a large zinc containing glycoprotein that occurs as a 400 kDa homodimeric structure and is present in follicular fluid. PAPP-A is believed to be released by granulosa cells, cleaving insulin-like growth factor binding protein 4 (IGFBP-4) and resulting in the release of insulin-like growth factor-2 (IGF-2). Although PAPP-A levels have been measured in human follicular fluid and its levels have been found to correlate with dominant follicle selection, little was known with regard to PAPP-A levels on resulting oocyte maturity and subsequent fertilization rate. The present inventor discovered that the level of PAPP-A protein or mRNA present in a non-pregnant female mammal's bodily fluid such as blood (especially serum or plasma), follicular fluid, urine, saliva, oral washings, or reproductive tract washings positively correlates to the state of oocyte maturation.

This invention therefore provides, for the first time, methods and kits for assessing follicular maturation and timing ovulation in a female mammal by analyzing the level of PAPP-A protein or mRNA present in a bodily fluid from the female. The same general methodology is also useful for monitoring the progression of oocyte maturation during the follicular phase of a reproductive cycle, therefore predicting the time of ovulation. The comparison of PAPP-A protein or mRNA level to a prior established control is also useful for determining changes in a female's reproductive fitness level and chances of a successful pregnancy, whether it is by natural means or with aid such as artificial insemination and IFV. This PAPP-A based novel approach serves at least these purposes: (1) to facilitate the insemination process by providing appropriate timing to carry out the process; (2) to facilitate an IVF procedure by providing appropriate time for administering an agent further promoting egg maturation (e.g., human chorionic gonadotropin or hCG) prior to harvest of eggs for use in IVF; and (3) to provide a general prediction of success rate in pregnancy including that in an IVF procedure.

II. Preparing Test Samples

A. Obtaining Samples

The first step of practicing the present invention is to obtain a sample from a female being tested, e.g., a follicular fluid sample or a blood sample, especially a serum or plasma sample, from a female patient for monitoring oocyte maturation using a method of the present invention. The specific methods for taking test samples vary depending on the site or sites where the samples are taken. Standard procedures routinely employed in hospitals or clinics are typically followed for this purpose. For example, collection of blood samples from a patient is performed on a daily basis in a medical office. An appropriate amount of sample, e.g., between 5 to 20 ml of peripheral blood, is collected and maybe stored according to standard medical laboratory testing procedure prior to further preparation.

Follicular fluid is usually obtained with informed consent at the time of follicle aspiration for in vitro fertilization (IVF) procedures and from regularly menstruating women as described previously (Chandrasekher et al., *J. Clin. Endocrinol. Metab.*, 1995, 80:2734 2739). Briefly, follicular fluid is first centrifuged to remove cellular components and can then be stored frozen at −20° C. until use.

B. Preparing Blood Samples for PAPP-A Detection

The serum or plasma of a blood sample from a female subject is suitable for the present invention and can be obtained by well known methods. For example, a blood sample can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum is obtained through centrifugation following blood clotting. Centrifugation is typically conducted at an appropriate speed, e.g., 1,500-3,000×g, in a chilled environment, e.g., at a temperature of about 4-10° C. Plasma or serum may be subject to additional centrifugation steps before being transferred to a fresh tube for measuring the PAPP-A protein or mRNA level. In certain applications of this invention, plasma or serum may be the preferred sample types. In other applications of the present invention, whole blood may be preferable. In yet other applications, other bodily fluids from a female subject, such as follicular fluid, reproductive tract washings, urine, or saliva, may be preferable.

III. Determining PAPP-A Level

A biological sample from a female subject is assessed for the level of PAPP-A, including level of PAPP-A protein or mRNA, in the practice of the present invention. Suitable biological samples include, but are not limited to, blood (especially serum or plasma), follicular fluid, urine, saliva, oral washings, and reproductive tract washings. Blood is a particularly useful biological sample.

A. Determining PAPP-A Protein Level

PAPP-A protein can be detected using a variety of immunological assays. In some embodiments, a sandwich assay can be performed by capturing PAPP-A from a test sample with an antibody having specific binding affinity for PAPP-A protein. PAPP-A then can be detected with a labeled antibody having specific binding affinity for PAPP-A. Alternatively, standard immunohistochemical techniques can be used to detect PAPP-A protein, using such antibodies. Circulating PAPP-A protein may be present in free form, or it may be present in a complex with proform of eosinophil major basic protein (proMBP). Antibodies having affinity for PAPP-A/proMBP complexes are available. See, for example, Qin et al., *Clin. Chem.*, 1997, 43(12):2323 2332. Monoclonal antibodies having specific binding affinity for PAPP-A, but not for PAPP-A/proMBP complexes, can be produced through standard methods. In plasma and serum, some percentage of PAPP-A is not complexed with proMBP, but rather exists as a noncomplexed PAPP-A dimer. Measurements of the fraction of uncomplexed PAPP-A using a monoclonal antibody that recognizes the uncomplexed form of PAPP-A only is different from measuring total PAPP-A with either polyclonal or monoclonal antibodies. Measurement of uncomplexed PAPP-A in serum samples potentially has a diagnostic value. Because proMBP functions as a inhibitor of PAPP-A activity, the amount of uncomplexed PAPP-A can also be estimated by measuring the PAPP-A activity of a given sample.

PAPP-A not complexed to proMBP can be produced in various ways, including recombinantly, or can be purified from a biological sample, and used to immunize animals. To produce recombinant PAPP-A, a nucleic acid sequence encoding PAPP-A polypeptide can be ligated into an expression vector and used to transform a bacterial or eukaryotic host cell. In general, nucleic acid constructs include a regulatory sequence operably linked to a PAPP-A nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. Such fusion proteins are often soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express PAPP-A protein can be produced by using expression vectors with the appropriate control elements and a selectable marker. For example, the eukaryotic expression vector pcDNA.3.1$^+$ (Invitrogen, San Diego, Calif.) is suitable for expression of PAPP-A in, for example, COS cells or HEK293 cells. Following introduction of the expression vector by electroporation, DEAE dextran, or other suitable method, stable cell lines are selected. In an expression system using pcDNA3.1$^+$ and HEK293 cells, yield of the protein was about 5 μg/ml. The secreted product was a dimer devoid of proMBP. Alternatively, PAPP-A can be transcribed and translated in vitro using wheat germ extract or rabbit reticulocyte lysate.

In eukaryotic host cells, a number of viral-based expression systems can be utilized to express PAPP-A. A nucleic acid encoding PAPP-A can be cloned into, for example, a baculoviral vector and then used to transfect insect cells. Alternatively, the nucleic acid encoding PAPP-A can be introduced into a SV40 retroviral or vaccinia based viral vector and used to infect host cells.

As described herein, recombinant PAPP-A (rPAPP-A) is immunoreactive against all available monoclonal antibodies in ELISA and in Western blotting. Recombinant PAPP-A is secreted as a homodimer of about 400 kDa; and after reduction yields monomers slightly smaller than the 200 kDa subunit from pregnancy serum PAPP-A because of a lower degree of glycosylation. rPAPP-A is active and cleaves IGFBP-4 in an IGF dependent manner.

PAPP-A can be purified, as described herein. For example, PAPP-A can be purified from HFCM by passing over iminodiacetic acid immobilized to Sepharose 6B loaded with $Zn^{+2}$. After elution of bound proteins with a stepwise decreasing pH gradient, the pH 5.0 fraction can be purified further by passing over a wheat gem agglutinin column. Bound proteins can be eluted with a Tris-salt solution, and then by N-acetylglucosamine. Alternatively, a heparin sepharose column can be used and PAPP-A is eluted with an increase in salt concentration to 1000 mM. Fractions containing PAPP-A, as measured with PAPP-A specific antibodies or with a specific protease activity assay, can be pooled, concentrated, then assessed by SDS polyacrylamide gel electrophoresis. In reducing SDS/PAGE, the molecular mass of PAPP-A monomer is approximately 200 kDa.

Various host animals can be immunized by injection of PAPP-A. Host animals include rabbits, chickens, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a PAPP-A polypeptide and standard hybridoma technology. In particular, monoclonal antibodies can be obtained by any technique that provides for the production of antibody molecules by continuous cell lines in culture such as described by Kohler, G. et al., Nature, 256:495 (1975), the human B-cell hybridoma technique (Kosbor et al., Immunology Today, 4:72 (1983); Cole et al., Proc. Natl. Acad. Sci. USA, 80:2026 (1983)), and the EBV-hybridoma technique (Cole et al., "Monoclonal Antibodies and Cancer Therapy" Alan R. Liss, Inc., pp. 77 96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

Antibody fragments that have specific binding affinity for PAPP-A polypeptide can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed. See, for example, Huse et al., Science, 246:1275 (1989). Once produced, antibodies or fragments thereof are tested for recognition of PAPP-A by standard immunoassay methods including ELISA techniques, radioimmunoassays and Western blotting. See, e.g., Short Protocols in Molecular Biology, Chapter 11, Green Publishing Associates and John Wiley & Sons, Edited by Ausubel, F. M et al., 1992. Antibodies having affinity for PAPP-A are identified in a positive selection. Antibodies identified in such a selection can be negatively selected against PAPP-A/proMBP, to identify antibodies having specific binding affinity for epitopes of PAPP-A that are not accessible in the specific complex of PAPP-A and proMBP. In some embodiments of this invention, the total PAPP-A protein level in a sample is measured regardless of the protein's association with proMBP. In other embodiments, the PAPP-A protein level in the PAPP-A/proMBP heterotetramer is used, as the PAPP-A/proMBP is the predominant form of PAPP-A and accounts for the vast majority of total PAPP-A protein level.

B. Determining PAPP-A mRNA Level

There are numerous methods for extracting mRNA from a biological sample. The general methods of mRNA preparation (e.g., described by Sambrook and Russell, Molecular Cloning: A Laboratory Manual 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a female test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of PAPP-A mRNA may be quantified. The preferred method for determining the mRNA level is an amplification-based method, e.g., by polymerase chain reaction (PCR).

Prior to the amplification step, a DNA copy (cDNA) of the PAPP-A mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, Adv. Clin. Chem. 33:201-235, 1998.

2. Other Quantitative Methods

The PAPP-A mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, Sambrook and Russell, supra), the presence of a band of the same size as the standard control is an indication of the presence of a target mRNA, the amount of which may then be compared to the control based on the intensity of the band. Alternatively, oligonucleotide probes specific to PAPP-A mRNA can be used to detect the presence of such mRNA species and indicate the amount of mRNA in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., Biotechniques 4:230, 1986; Haase et al., Methods in Virology, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3H$, $^{125}I$, $^{35}S$, $^{14}C$, or $^{32}P$, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

IV. Establishing a Standard Control

In order to establish a standard control, a group of female subjects without any known fertility disorders is first be selected. These individuals may optionally have the same or similar age, biological features (e.g., ethnic background), and/or medical history. The fertility status of the selected individuals should be confirmed by well established, routinely employed methods, including but not limited to, X-ray, CT-scan, ultrasound, blood testing, and review of medical history.

Furthermore, the selected group of individuals without fertility disorders should be of a reasonable size, such that the average amount of PAPP-A protein or mRNA calculated from the group can be reasonably regarded as representative of the normal or average amount PAPP-A among the general population of healthy, fertile females of the species. Preferably, the selected group comprises at least 10 subjects.

In the alternative, a baseline level of PAPP-A protein or mRNA level can also be established as a standard control for a particular individual to indicate that individual's baseline level of oocyte maturation at a particular time (e.g., a particular day) during the reproductive cycle. This is particular useful in the context of determining any change over time in the state of the individual's reproductive fitness, which can predict the chance of pregnancy, either by natural or artificial insemination, or by in vitro fertilization.

Once an average value is established for the amount of PAPP-A protein or mRNA based on the individual values found in each individual of the selected group, this values is considered a standard for the PAPP-A protein or mRNA level for this type of sample, which may be limited to the specific bodily fluid, subjects' age, or time during the reproductive cycle. Any biological sample, e.g., a serum sample, that contains a similar amount of PAPP-A protein or mRNA can thus be used as a standard control. A solution containing PAPP-A protein or mRNA at a concentration of the established average of PAPP-A protein or mRNA can also be artificially assembled and serve as a standard control.

V. Assessing Oocyte Maturation State

Once the level of PAPP-A protein or mRNA is determined from a test sample, the state of oocyte maturation in the female being tested can then be assessed. In general, a higher level of PAPP-A level indicates a more advanced state of oocyte maturation during the female's cycle of follicular development and maturation. Monitoring the state of oocyte maturation by monitoring changes in the amount of PAPP-A protein or mRNA in a suitable bodily fluid (e.g., serum) over a time period, especially close to expected peak time of oocyte maturation, can provide a time frame for insemination or for harvesting eggs at top maturity level so as to enhance the likelihood of pregnancy. For instance, a woman's serum PAPP-P level can be monitored through the period of five days starting just prior to the expected time of ovulation. As follicular maturation progresses, the PAPP-A level will continue to increase, until the oocyte maturity reaches its peak. At this point the PAPP-A level will begin to decrease and such decrease provides an indication that the reproductive cycle is now at the point of transitioning from the follicular phase to luteal phase, and that it is the appropriate time (e.g., within 24 to 36 hours of the first detected decrease after at least 2 or 3 days of continuous increase) to either perform insemination by natural or artificial means, or to promote final maturation of the follicles (e.g., by administration of chorionic gonadotropin (such as hCG) or luteinizing hormone) and to extract mature eggs from the follicles for IVF procedure.

Monitoring and comparing PAPP-A level to a standard control can also indicate a better quality, and therefore a higher rate of success to achieve pregnancy, either by natural or artificial means of insemination, or by in vitro fertilization. For instance, if a particular woman's PAPP-A level is substantially lower than the control level, i.e., the average level among healthy fertile women of similar age at the similar or identical time during the menstrual cycle, then the woman's chance of becoming pregnant is below average in a manner correlated with the deficiency in PAPP-A level: the larger the decrease from the control level, the less the chance of a successful pregnancy. Similarly, the PAPP-A level can also be compared with a previously established control or baseline level for the same individual to reflect changes in female fertility over time. For instance, the serum PAPP-A level for a particular woman is established on the 10th day into her menstrual cycle. 30 months later her serum PAPP-A level can be measured again on day 10 of her menstrual cycle and compared with the control level, i.e., the level detected from 30 months ago. An increase or decrease from the previously established level will indicate a higher or lower fertility, respectively, from 30 months ago.

VI. Kits

The invention provides compositions and kits for practicing the methods described herein to assess the state of oocyte maturation in a female subject, which can be used for various purposes such as providing a time frame for natural or artificial insemination, as well as for administering additional agent(s) to a female to further oocyte maturation before harvesting eggs for in vitro fertilization.

Kits for carrying out the immunoassays for determining PAPP-A protein level typically include a detection agent that comprises an antibody (a polyclonal or monoclonal antibody, or an antiserum) that specifically binds to the PAPP-A protein. Optionally, a detectable label is conjugated to the detection agent for indicating the presence of the agent and therefore the PAPP-A protein. In some cases, the kits may include multiple antibodies for detection purposes. For examples, a primary antibody and a secondary antibody may be included in the kits, with the primary antibody having a binding specificity for the PAPP-A protein, and the secondary antibody having a binding specificity for the primary antibody and having a detectable label or moiety.

Kits for carrying out assays for determining PAPP-A mRNA level typically include at least one oligonucleotide useful for specific hybridization with the PAPP-A coding sequence or complementary sequence. Optionally, this oligonucleotide is labeled with a detectable moiety. In some cases, the kits may include at least two oligonucleotide primers that can be used in the amplification of PAPP-A mRNA by PCR, particularly by RT-PCR.

Typically, the kits also provide instruction manuals to guide users in analyzing test samples and assessing the state of oocyte maturation in a female test subject.

EXAMPLES

The following examples are provided by way of illustration only and not by way of limitation. Those of skill in the art will readily recognize a variety of non-critical parameters that could be changed or modified to yield essentially the same or similar results.

Example 1

PAPP-A Level in Follicular Fluid and Human Follicle Maturation

The objective of this study was to examine PAPP-A levels in human follicular fluid (hFF) obtained from women undergoing assisted reproductive technology (ART). The amount of PAPP-A protein measured in hFF ranged from a low of 270.8 ng/mL to a high of 7275.5 ng/mL. Polynomial regression analysis revealed a significant binomial relationship ($R^2=0.523$; $F=5.483$; $P<0.05$) between PAPP-A protein content and the day hCG was given. Polynomial regression analysis revealed a significant binomial relationship ($R^2=0.610$; $F=7.806$; $P<0.05$) between PAPP-A protein content and the total dose of follicle-stimulating hormone (FSH) was given. Relational trends were observed between PAPP-A protein level and egg maturity rate as well as between PAPP-A protein level and fertilization rate. These data demonstrate that not only is PAPP-A protein present in human follicular fluid but also PAPP-A levels are correlated with follicular maturation.

Figure 2A:
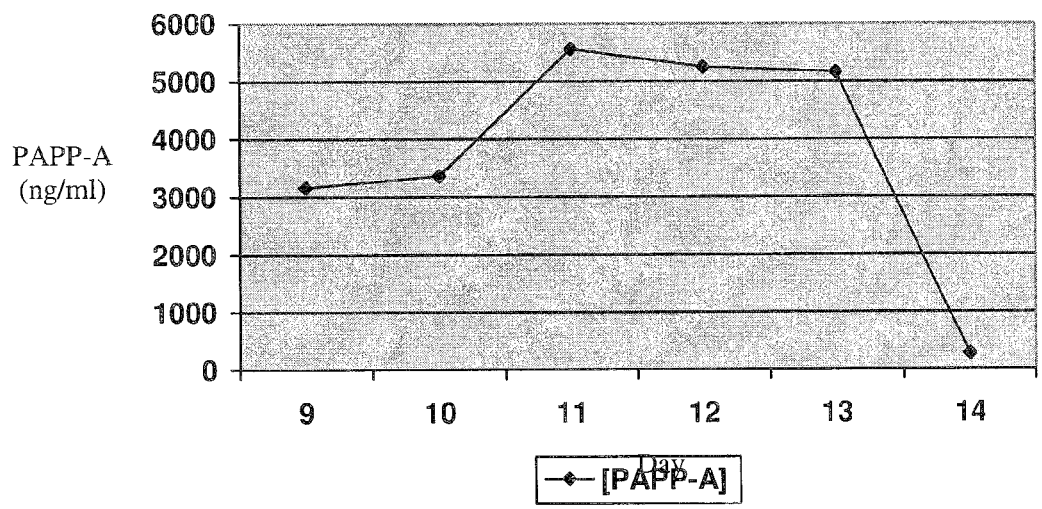
FIG. 2A shows mean PAPP-A levels in follicular fluid and day of hCG.
Figure 2B:
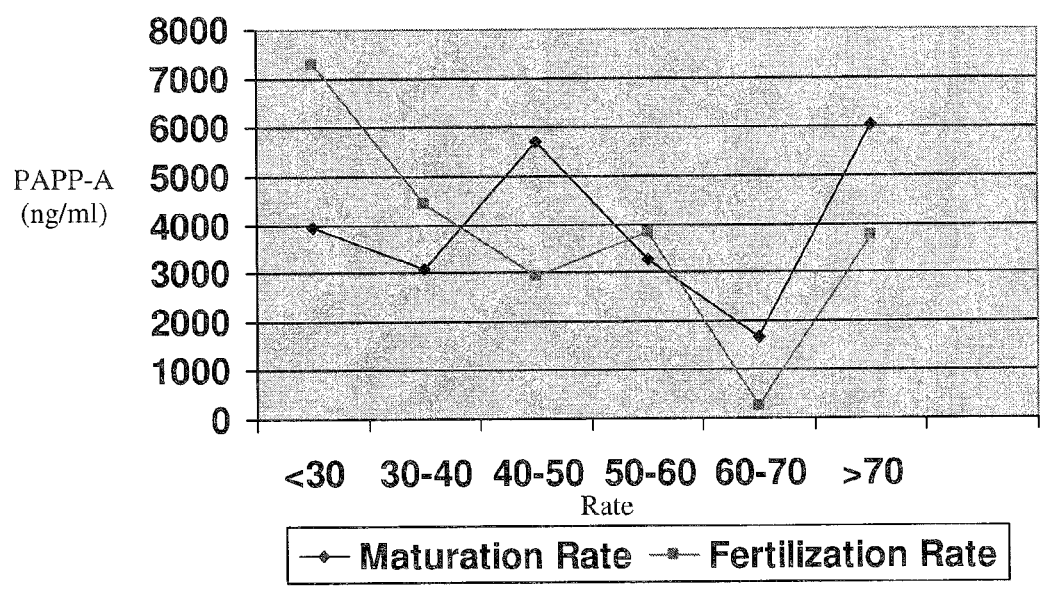
FIG. 2B shows same PAPP-A levels and subsequent relationship with follicle maturation and fertilization rate.
Figure 2C:
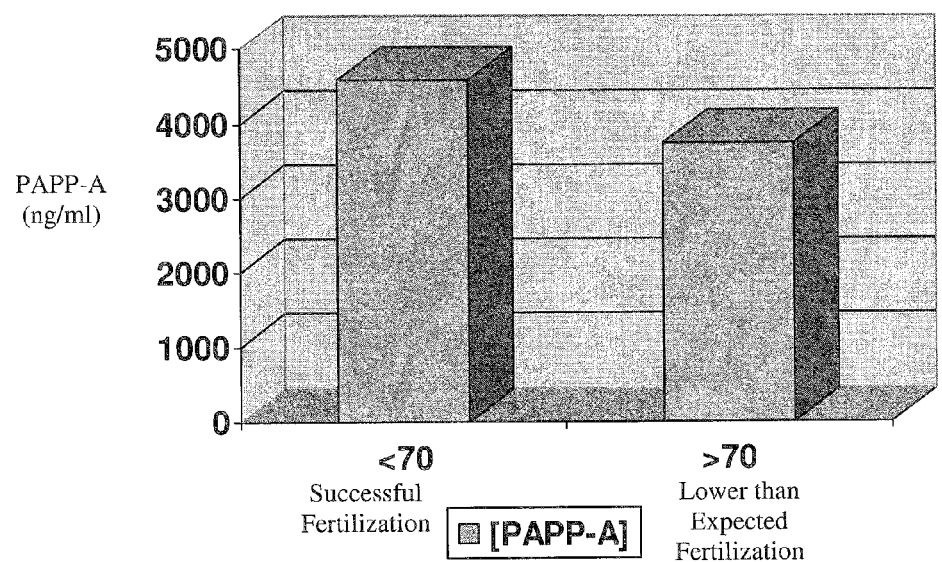
FIG. 2C shows significant difference of PAPP-A levels in follicular fluid and successful (>70%) fertilization rate vs. lower than expected (<70%).

Detailed data from each individual patient participated in this study are shown in FIG. 1, and are summarized in Table 1 and FIG. 2.

TABLE 1

| Patient ID | PAPP-A [ng/mL] | FSH Dose-Total | hCG Day | Ova Maturity Rate | Fertilization Rate |
|---|---|---|---|---|---|
| 11750 | 270.8 | 4500 | 14 | 0.60 | 0.67 |
| 11775 | 2418.7 | 525 | 9 | 0.33 | 0.80 |
| 11648 | 2920.6 | 1050 | 10 | 0.25 | 0.41 |
| 11689 | 3046.2 | 3825 | 13 | 0.67 | 0.79 |
| 11518 | 3253.8 | 1225 | 9 | 0.52 | 0.79 |
| 11522 | 3267.7 | 800 | 9 | 0.50 | 0.92 |
| 11747 | 3329.9 | 2025 | 10 | 0.20 | 0.30 |
| 11809 | 3731.3 | 925 | 9 | 0.38 | 0.91 |
| 11005 | 3837.4 | 1000 | 10 | na | 0.56 |
| 11619 | 4797.3 | 2550 | 12 | 1.00 | 0.75 |
| 11184 | 5559.0 | 2925 | 11 | 0.27 | 0.36 |
| 10253 | 5700.1 | 3050 | 12 | 0.44 | 0.71 |
| 11702 | 7275.5 | 4500 | 13 | 1.00 | 0.20 |

Data has not been normalized to consider patient demographics (e.g., age), mode of fertilization, etc.

As shown in FIG. 2, the PAPP-A protein level in follicular fluid changes around the time of optimal follicular maturation (2A), and correlate with maturation (2B) and subsequent fertilization rate (2C). Data is a mean summarization of all samples assayed for PAPP-A; axis-a is day of stimulation cycle; axis-Y is amount of PAPP-A [ng/mL].

Example 2

PAPP-A Levels in Serum

Figure 4A:
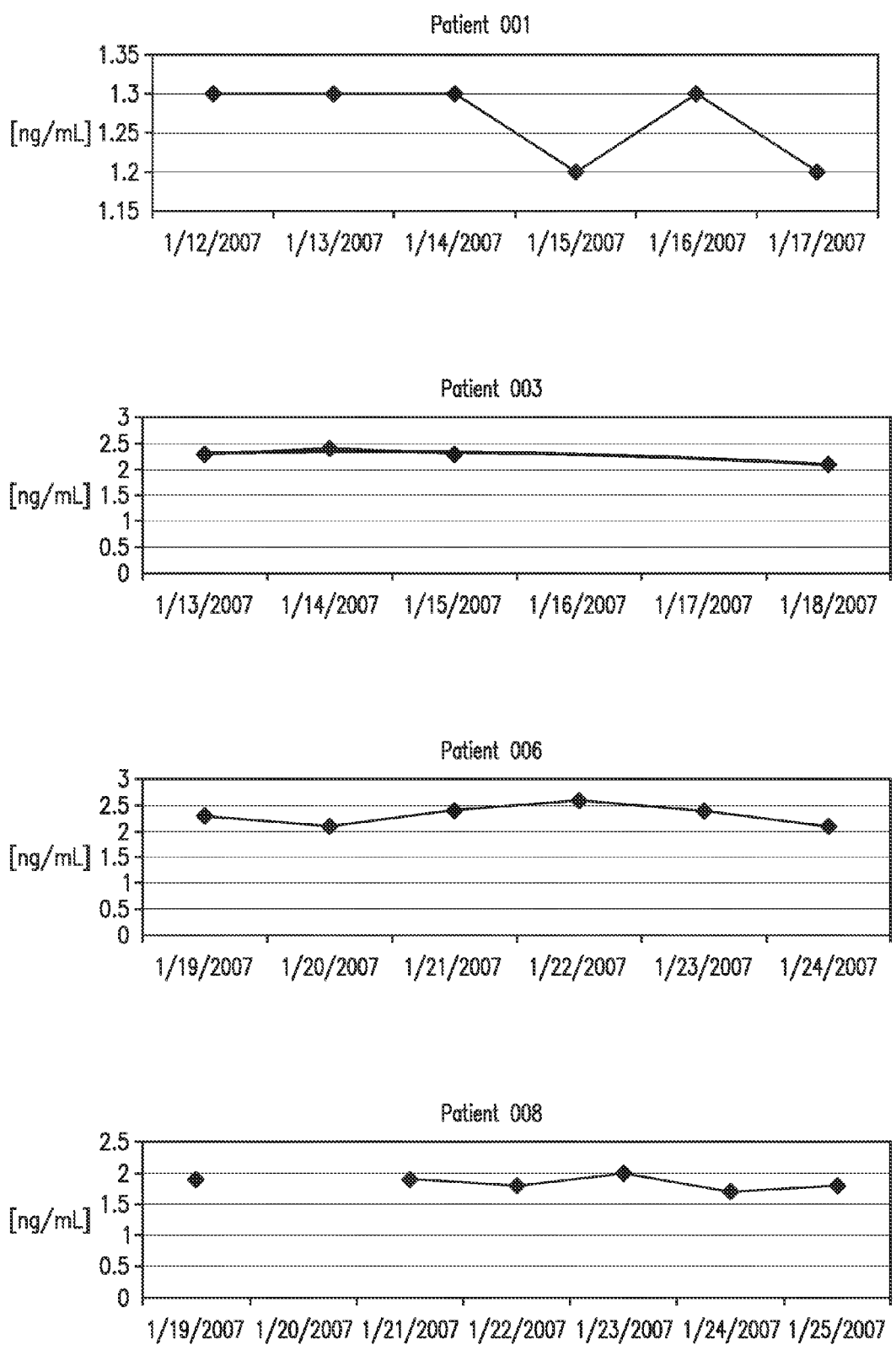
Figure 4D:
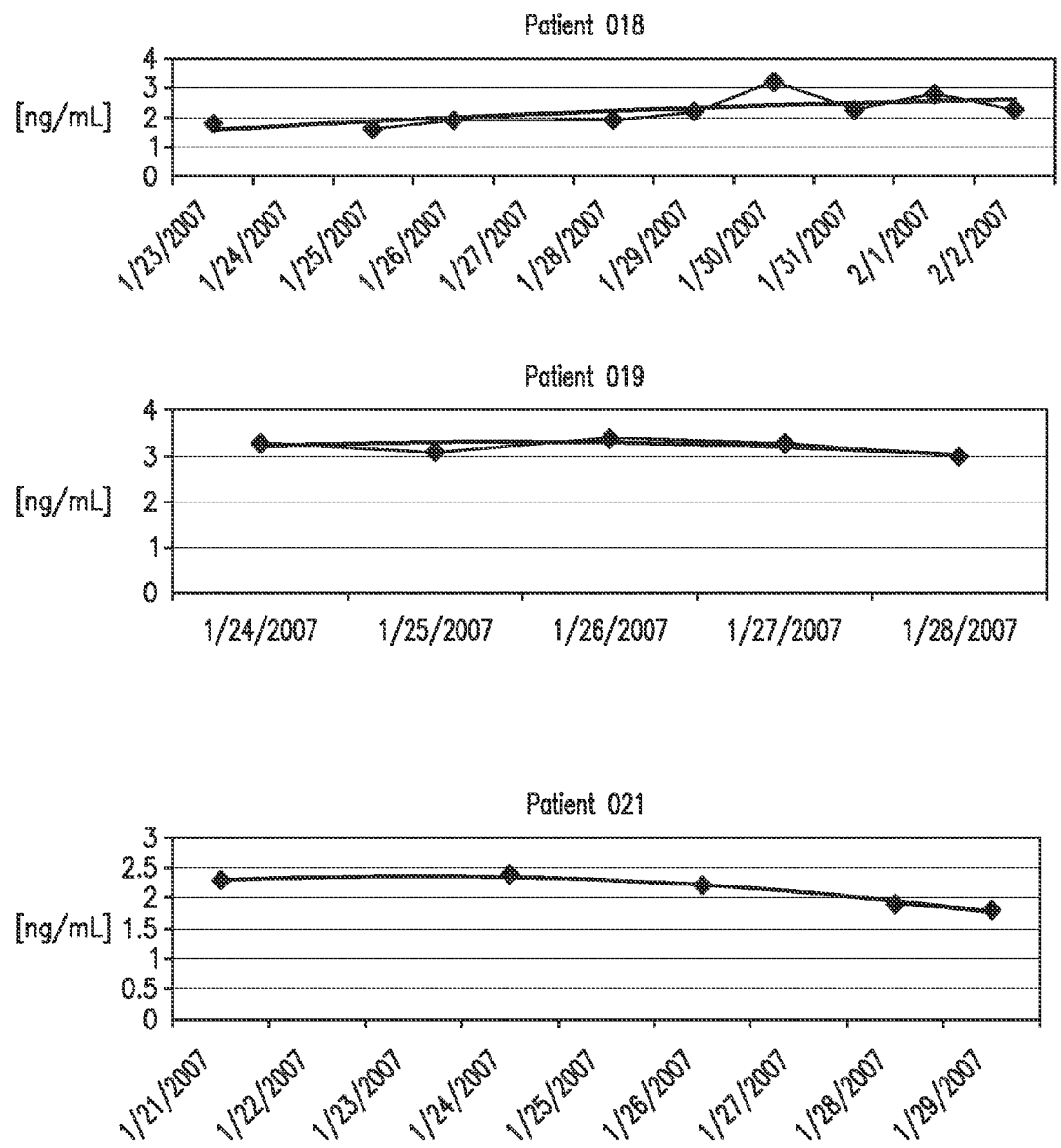
Figure 5A:
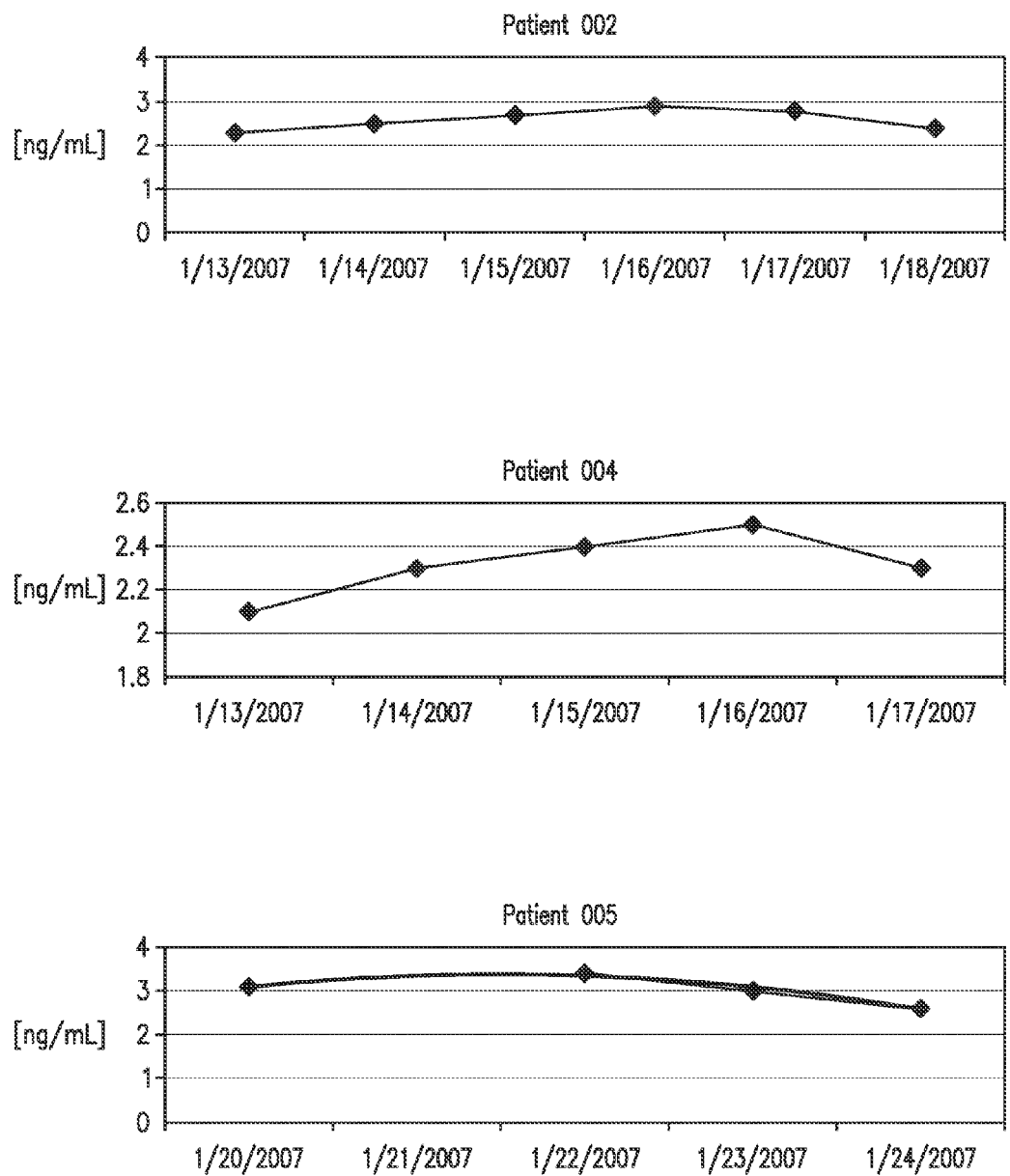
FIGS. 5A-5D show serum PAPP-A levels in another pool of women over a period of at least 5 days.
Figure 5B:
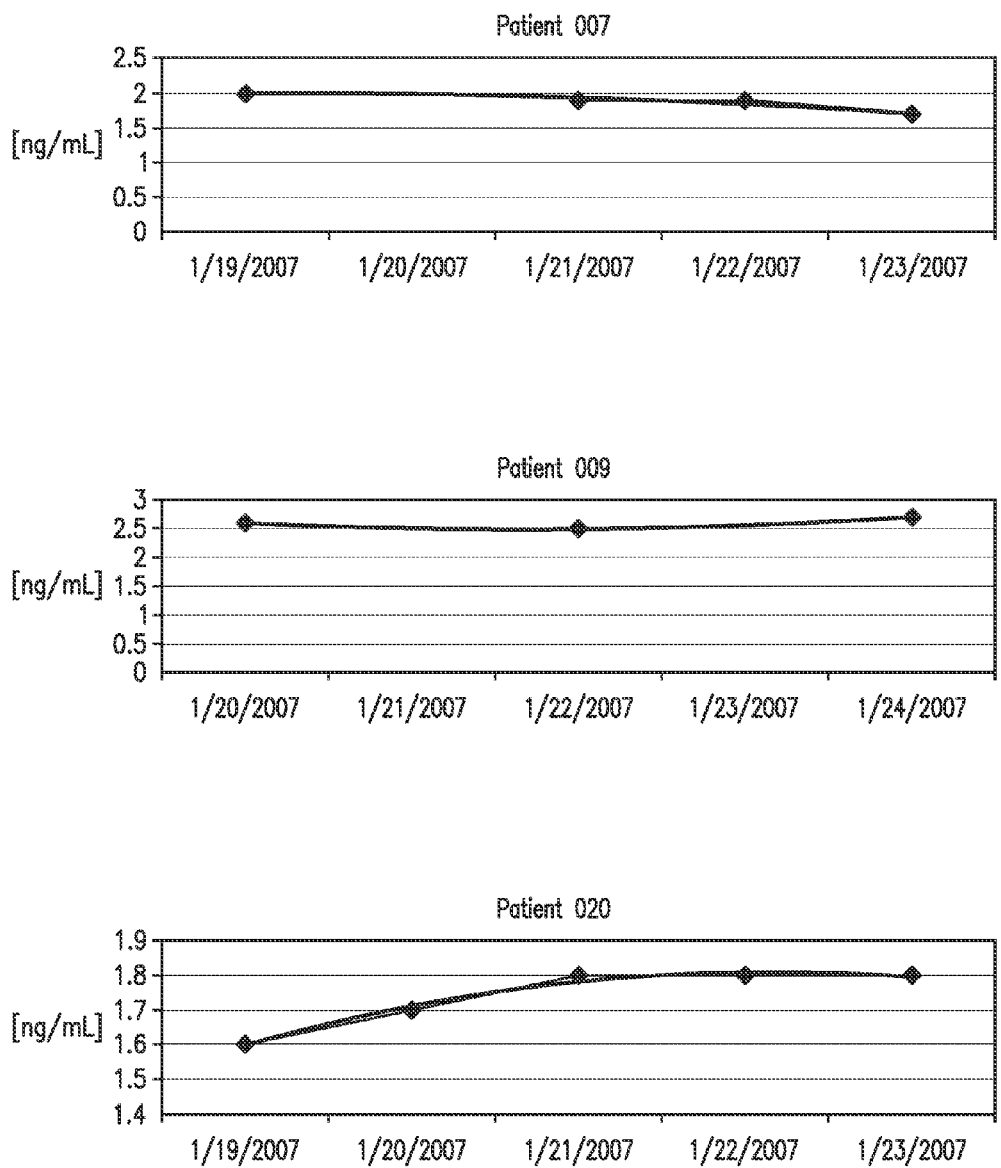
Figure 5C:
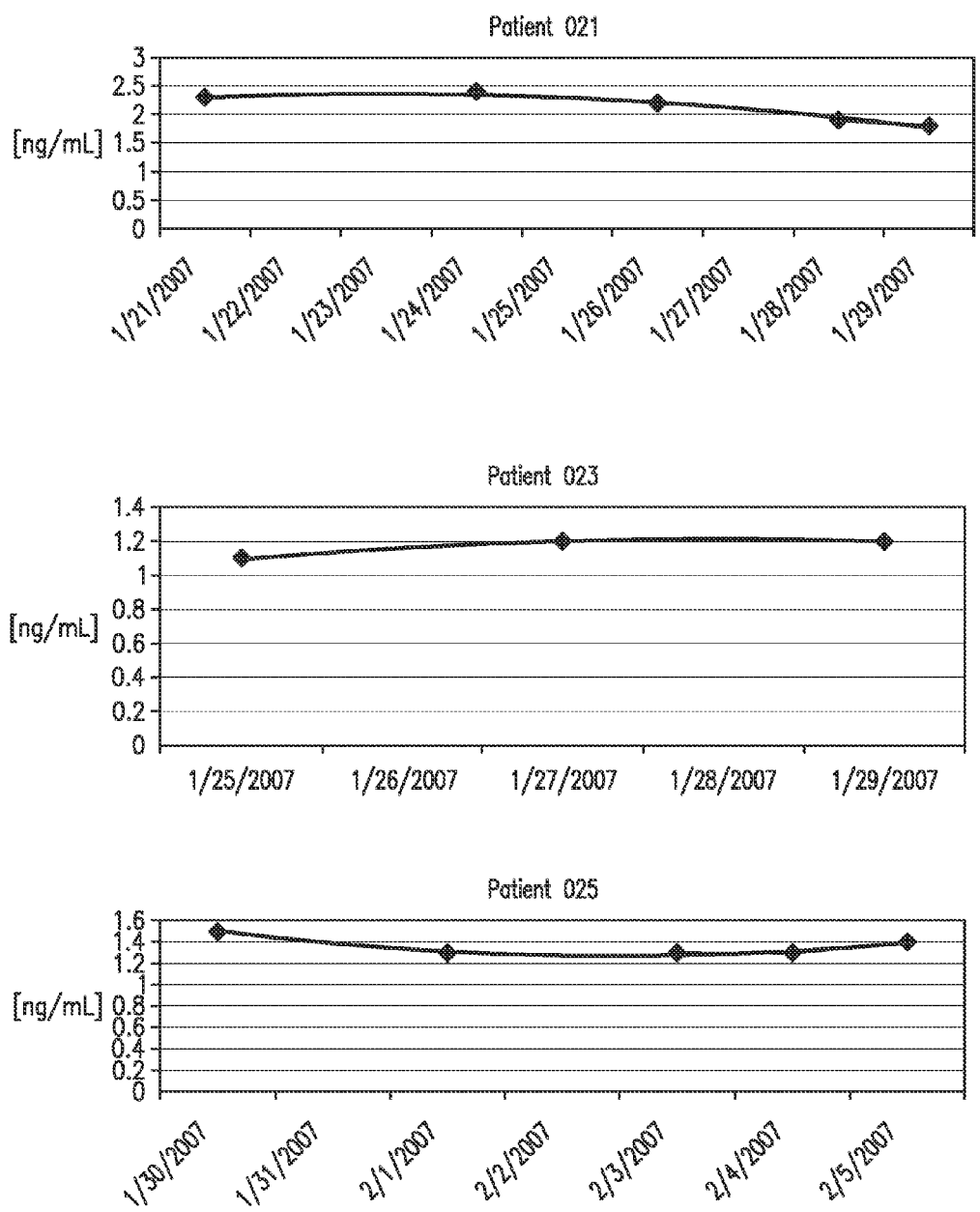
Figure 5D:
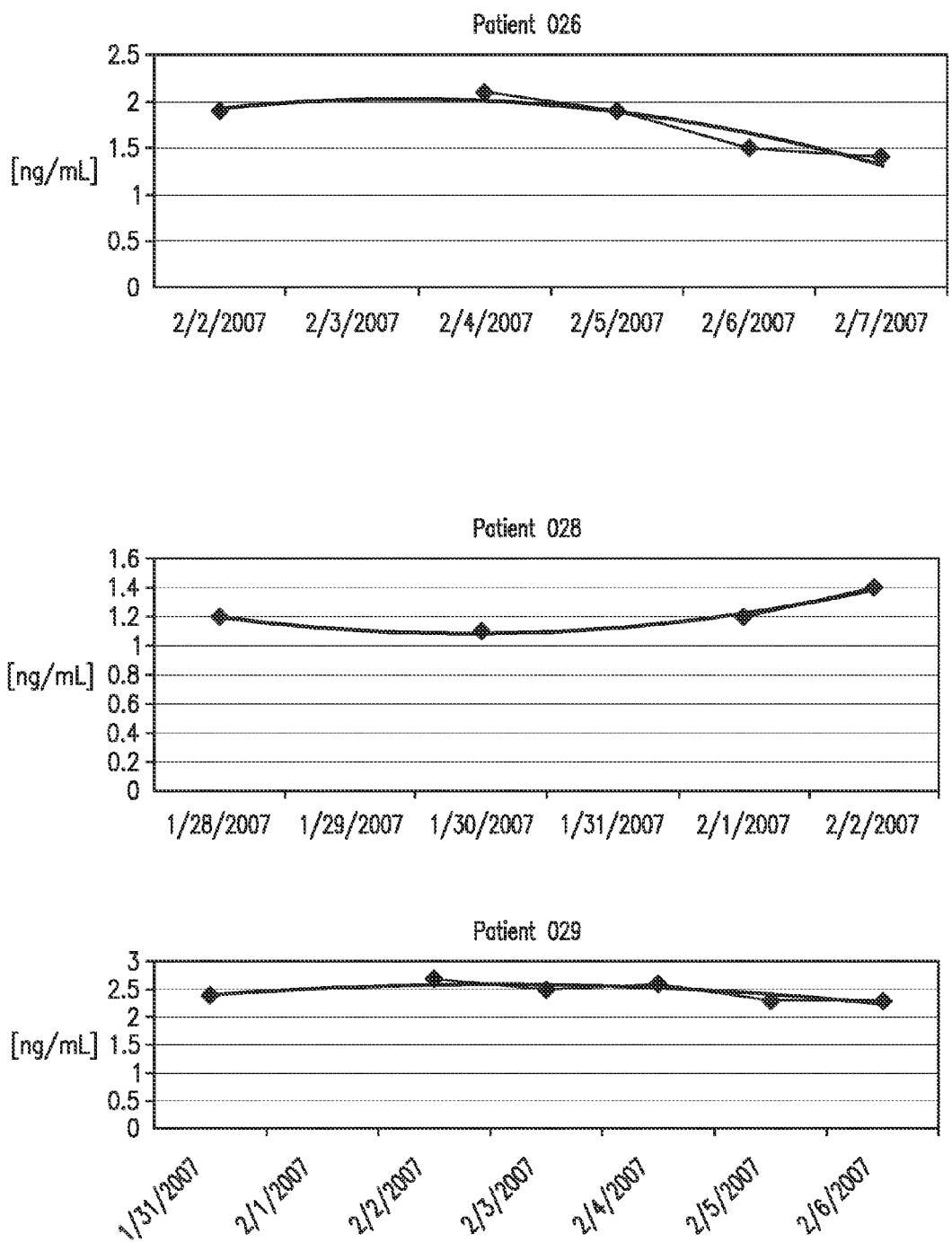

This study examined the levels of PAPP-A protein in women's serum and their correlation with follicular maturation and fertilization rate. FIG. 3 provides the PAPP-A protein levels in the women's serum as measured everyday or every other day for a period of at least 4 days. FIG. 4 presents the same data in a graphic form. The graph for patient 016 is an example in which a patient whose PAPP-A levels change in accordance with follicle maturity; the graph for patient 013 is an example where no change in maturation was found, as confirmed by the corresponding oocyte maturation and fertilization results. Red colored line is linear regression line for anticipated changes.

The serum PAPP-A protein levels were also tested among women undergoing ovulation induction for insemination. FIG. 5 shows PAPP-A serum levels in these women over a period of at least 5 days. Time of insemination was determined by monitoring urine LH spike, when a positive LH surge was noted then insemination was scheduled for that day and/or the following day.

All patents, patent applications, and other publications, including GenBank Accession Numbers, cited in this application are incorporated by reference in the entirety for all purposes.

What is claimed is:

1. A method for assessing oocyte maturation in a female, comprising detecting pregnancy-associated plasma protein (PAPP-A) level in a bodily fluid from the female, wherein the PAPP-A level of the female is detected daily for a least three consecutive days;

comparing the PAPP-A level with a control to assess oocyte maturation in the female, the control comprising a previously established baseline PAPP-A level for the bodily fluid of the same female or an average PAPP-A level for the bodily fluid from a healthy fertile non-pregnant female, wherein an increase in the PAPP-A level compared to the control indicates a more advanced state of oocyte maturation and a decrease in the PAPP-A level compared to the control indicates a lesser state of oocyte maturation; and administering a hormone which induces oocyte maturation to the female within 36 hours after the PAPP-A level in the female exhibits a decrease after continuous increase for at least two consecutive days, the hormone being administered to the female in an amount sufficient to induce final maturation of oocytes in the female.

2. The method of claim 1, wherein the PAPP-A level is the PAPP-A protein level of total PAPP-A, PAPP-A homodimer, or PAPP-A/proform of eosinophil major basic protein (proMBP) heterodimer.

3. The method of claim 1, wherein the bodily fluid is follicular fluid, serum or plasma.

4. The method of claim 1, wherein the control is the average PAPP-A level for the body fluid from a healthy fertile non-pregnant female.

5. The method of claim 1, wherein the control is a previously established baseline level of PAPP-A for the bodily fluid from the same female.

6. The method of claim 1, wherein detecting the PAPP-A level is performed in an immunoassay using an anti-PAPP-A antibody or antigen binding fragment thereof.

7. The method of claim 6, wherein the anti-PAPP-A antibody is a polyclonal antibody.

8. The method of claim 6, wherein the anti-PAPP-A antibody is a monoclonal antibody.

9. The method of claim 6, wherein the antigen binding antibody fragment is a Fab or F(ab')$_2$.

10. The method of claim 6, wherein the anti-PAPP-A antibody or antigen binding fragment thereof comprises a detectable label or moiety.

11. The method of claim 1, wherein the PAPP-A level from each day is compared to monitor changes in oocyte maturation in the female, a higher PAPP-A level indicating a more advanced state of oocyte maturation.

12. The method of claim 1, wherein the hormone is chorionic gonadotropin (CG) or luteinizing hormone (LH).

13. The method of claim 1, wherein the hormone is administered within 24 hours after the PAPP-A level shows a decrease after continuous increase for at least two consecutive days.

14. The method of claim 13, wherein the female is a human female and the CH or LH is human chorionic gonadotropin (hCG) or human luteinizing hormone (hLH).

15. The method of claim 1, further comprising, subsequent to administering the hormone to the female, collecting mature oocytes from the female.

16. The method of claim 15, wherein the female is a human female and the CH or LH is human chorionic gonadotropin (hCG) or human luteinizing hormone (hLH).

17. The method of claim 1, wherein the female is a human female and the hormone is human chorionic gonadotropin (hCG) or human luteinizing hormone (hLH).

18. A method for assessing oocyte maturation in a female, comprising
    detecting pregnancy-associated plasma protein (PAPP-A) level in a bodily fluid from the female, wherein the PAPP-A level of the female is detected daily for a least three consecutive days;
    comparing the PAPP-A level with a control to assess oocyte maturation in the female, the control comprising a previously established baseline PAPP-A level for the bodily fluid of the same female or an average PAPP-A level for the bodily fluid from a healthy fertile non-pregnant female, wherein an increase in the PAPP-A level compared to the control indicates a more advanced state of oocyte maturation and a decrease in the PAPP-A level compared to the control indicates a lesser state of oocyte maturation; and
    inseminating the female within 36 hours after the PAPP-A level in the female exhibits a decrease after continuous increase for at least two consecutive days.

19. The method of claim 18, wherein the PAPP-A level is the PAPP-A protein level of total PAPP-A, PAPP-A homodimer, or PAPP-A/proMBP heterodimer.

20. The method of claim 18, wherein the bodily fluid is follicular fluid, serum or plasma.

21. The method of claim 18, wherein the control is the average PAPP-A level for the body fluid from a healthy fertile non-pregnant female.

22. The method of claim 18, wherein the control is a previously established baseline level of PAPP-A for the bodily fluid from the same female.

23. The method of claim 18, wherein detecting the PAPP-A level is performed in an immunoassay using an anti-PAPP-A antibody or antigen binding fragment thereof.

* * * * *